Figure 1:
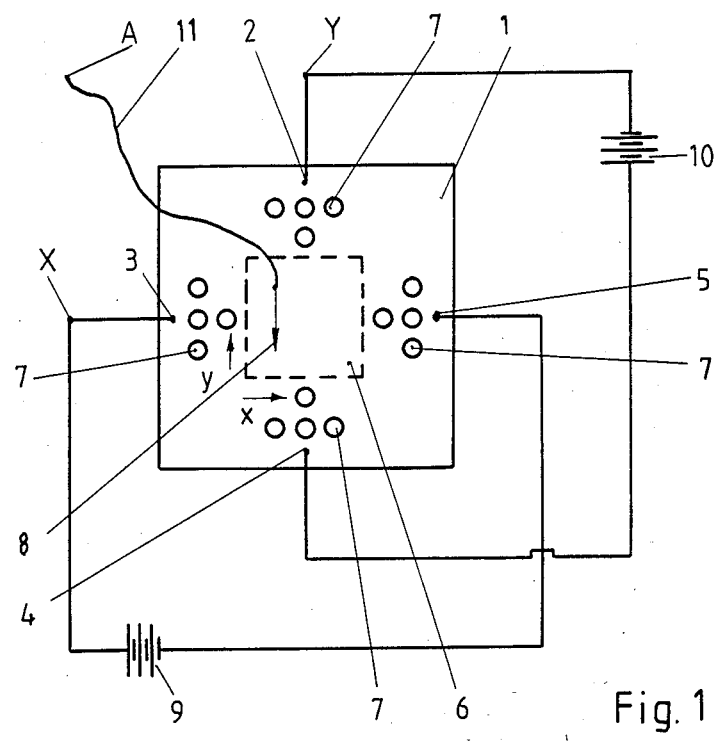

United States Patent [19]

Meyer et al.

[11] Patent Number: 4,587,977
[45] Date of Patent: May 13, 1986

[54] MEASURING DEVICE FOR DETERMINING THE LOCATION OF A STYLUS

[76] Inventors: Georg Meyer, Emilienstr. 11; Heinz dal Ri, Tuckmannweg 2, both of 3400 Göttingen, Fed. Rep. of Germany

[21] Appl. No.: 553,487

[22] Filed: Nov. 18, 1983

[30] Foreign Application Priority Data

Nov. 27, 1982 [DE] Fed. Rep. of Germany ....... 3243954

[51] Int. Cl.⁴ .............................................. A61B 5/10
[52] U.S. Cl. .................................. 128/777; 33/513; 178/20
[58] Field of Search ............... 128/691, 692, 713, 736, 128/777, 774; 33/1 M, 174 D, 512-514; 178/18

[56] References Cited

U.S. PATENT DOCUMENTS

| | | | |
|---|---|---|---|
| 3,078,584 | 2/1963 | Cohn | 33/174 D |
| 3,256,523 | 6/1966 | Pietro | 33/174 D |
| 3,530,241 | 9/1970 | Ellis | 178/18 |
| 3,699,439 | 10/1972 | Turner | 178/18 |
| 3,726,269 | 4/1973 | Webster, Jr. | 128/713 |
| 4,198,539 | 4/1980 | Pepper, Jr. | 178/18 |
| 4,214,122 | 7/1980 | Kley | 178/18 |
| 4,328,620 | 5/1982 | Mack et al. | 33/174 D |
| 4,419,672 | 12/1983 | Hird | 33/1 M |
| 4,459,109 | 7/1984 | Radke | 128/777 |
| 4,492,819 | 1/1985 | Rodgers et al. | 33/1 M |

FOREIGN PATENT DOCUMENTS 612957 11/1960 Italy ..................................... 33/1 M Primary Examiner—Kyle L. Howell
Assistant Examiner—Ruth S. Smith
Attorney, Agent, or Firm—Max Fogiel

[57] ABSTRACT

Planar electric measuring device that determines the site at which a stylus rests on it and apparatus for multi-dimensional measuring of jaw or tempero-mandibular movement. This is a simple means of obtaining precise measurements. An electrically conductive surface is positioned below and in contact with the stylus, has connection electrodes applied to it more or less in the form of points, and has perforations in the vicinity of the electrodes.

14 Claims, 4 Drawing Figures

MEASURING DEVICE FOR DETERMINING THE LOCATION OF A STYLUS

The present invention concerns a planar electric measuring device that determines the site at which a stylus rests on it and apparatus for multidimensional measurement of jaw or tempero-mandibular movement with an upper frame that is applied to a patient's head and a lower frame that is applied to the patient's mandible.

Devices of this type are known, from German Offenlegungsschrift No. 2 934 750 for example. They are employed to measure the tempero-mandibular joint and its movement, especially to trace the path followed by the condyle. They usually utilize a trace plates onto which the path is transcribed by a measuring or tracing stylus mounted on the lower frame. German Offenlegungsschrift No. 2 439 125 discloses, instead of the trace plate an electric pickup that operates in conjunction with the stylus. The pickup described in that document is essentially a wire grid. Induced currents occur at its nodes and are processed by an evaluating circuit and displayed. The accuracy, however, that can be attained with such an apparatus is much too limited for medical purposes.

The object of the present invention is accordingly a measuring device that determines the site at which a stylus rests on it and apparatus, equipped with such a measuring device, that is intended for multidimensional measurement of jaw or tempero-mandibular movement, that is highly accurate, and that yields precise and reproducible results with little expenditure for the associated evaluating circuitry.

This object is attained in accordance with the invention with an electrically conductive surface that is positioned below and in contact with the stylus, that has connection electrodes applied to it more or less in the form of points, and that has perforations in the vicinity of the electrodes. Such a device is extraordinarily accurate and, since it functions essentially like a potentiometer, expenditure for the associated evaluating circuitry will be low. The device can be connected directly to an X-Y plotter without intermediate amplifiers or similar components, which is naturally cost-effective. The geometric dimensions of the measuring device and conductive surface and the placement and dimensions of the electrodes and perforations are preferably selected to yield a predetermined system of equipotential lines on the conductive surface. No downstream electric circuits to linearize the results are necessary, which also contributes to simplicity and precision.

It is practical for the electrodes to be positioned in pairs with the measuring surface between them and with the lines connecting each pair intersecting. This is a simple way of obtaining two-dimensional measurements.

It is practical for the electrodes and associated perforations in the conductive surface to be positioned symmetrically, which facilitates manufacture. The conductive surface can be made out of resistive film with the perforations punched out of it for example.

It is practical to utilize the measuring device in apparatus for multidimensional measurement of jaw or tempero-mandibular movement with the measuring device mounted on its upper frame, which is applied to the patient's head, and the stylus mounted on its lower frame, which is applied to the patient's mandible. This is a simple and accurate means of obtaining measurements of the path followed by the tempero-mandibular joint. It is preferable for the measuring device to be mounted on the upper frame in such a way that it can be rotated and displaced. It can then be easily positioned as necessary to obtain the measurements in each case so that no subsequent conversion of the results into another coordinate system is necessary. It is practical to attach the measuring device to a plate on the upper frame with magnets.

Figure 2:
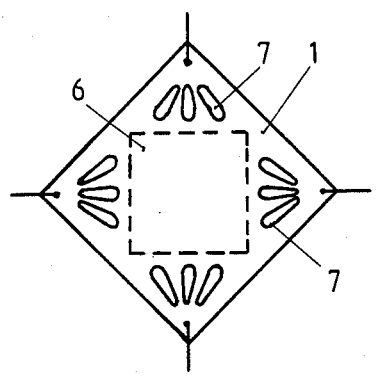
Figure 3:
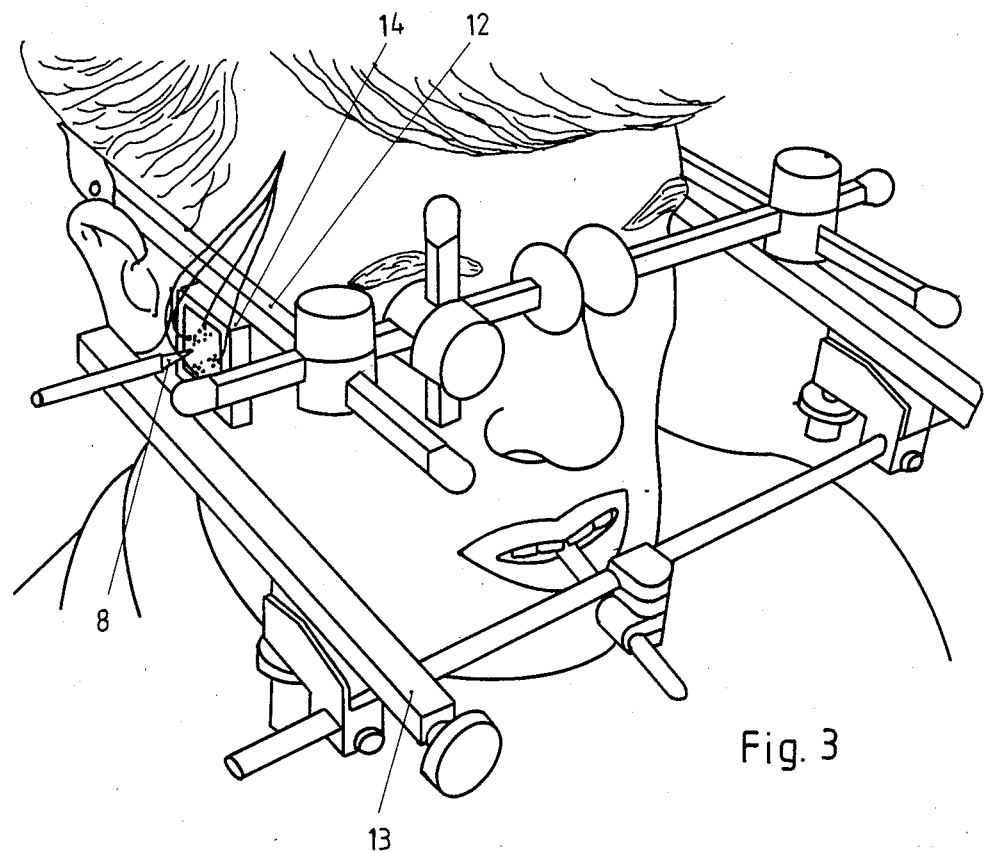
Figure 4:
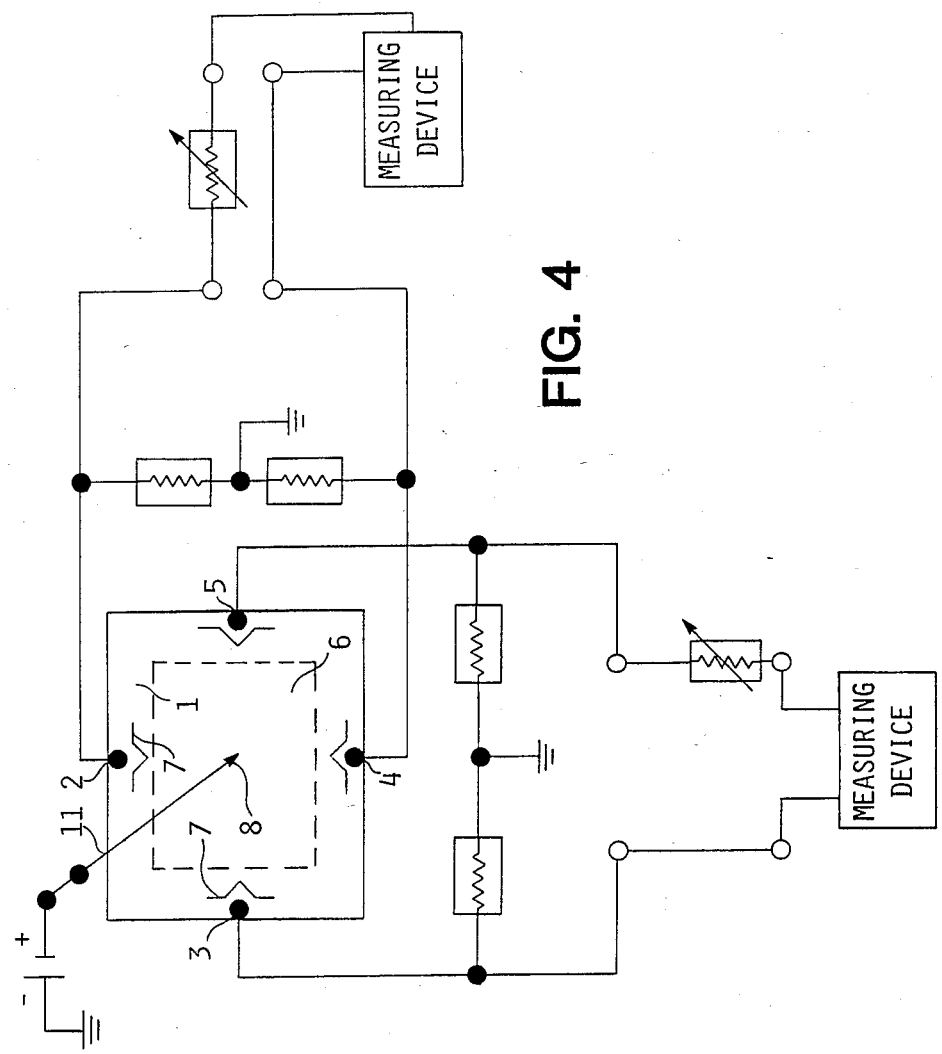

Some preferred embodiments of the invention will now be described with reference to the attached drawings, wherein FIG. 1 is a top view of a measuring device connected to an electric circuit, FIG. 2 is a top view of another embodiment, FIG. 3 is a perspective view of an apparatus applied to a patient's head to determine the paths followed by the moving tempero-mandibular joint, and FIG. 4 is a top view of another embodiment of the measuring device.

FIG. 1 is a top view of the measuring device, which consists essentially of a conductive surface 1 or layer mounted on a base plate. Conductive surface 1 may consist of a resistive film. Although the surface in the embodiment illustrated is square, it can have another shape depending on the purpose for which it is employed. Four electrodes 2, 3, 4, and 5 in the shape of points are mounted at the edge of conductive surface 1. The electrodes are mounted in opposing pairs with a measuring surface 6 between them. Between electrodes 2, 3, 4, and 5 and measuring surface 6 there are perforations 7 in conductive surface 1 that ensure a predetermined system and distribution of equipotential lines on measuring surface 6. A stylus 8, illustrated only schematically in FIG. 1, rests on and can travel over measuring surface 6.

The measuring device is connected to an electric circuit, the simplest form of which is schematically illustrated in FIG. 1. Each pair of opposing electrodes 2 and 4 and 3 and 5 is connected to voltage source 9 and 10 respectively. Stylus 8, which is in contact with measuring surface 6, is connected to a line 11. Voltages that depend on the position of stylus 8 on measuring surface 6 can be detected between connection points A and X or A and Y. The voltage between points A and X corresponds to the X coordinates of stylus 8 and that between points A and Y to its Y coordinates. The voltages between these points accordingly represent the instantaneous position of stylus 8 on measuring surface 6. Since the voltages vary continuously with the displacement of the stylus, a high level of precision is ensured. The voltages can be directly exploited to control an X-Y plotter without special amplifiers or linearization circuits.

Especially significant to the measuring device are the perforations in electrically conductive surface 1. In the embodiment illustrated in FIG. 1 there is a group of perforations 7 in front of each electrode 2, 3, 4, and 5. The perforations consist of circular recesses arranged in a triangle. This particular arrangement of perforations in front of the electrodes results in a desired distribution of equipotential lines on measuring surface 6. Undesired distortions can be minimized. FIG. 2 illustrates another embodiment of the measuring device. It differs from the first embodiment primarily in the arrangement of perforations 7 in front of the electrodes. The electrodes themselves are positioned in the corners of a square area. The measuring device in this embodiment can be smaller in relation to a measuring surface 6 of the same size.

FIG. 3 illustrates apparatus for multidimensional measurement of jaw or tempero-mandibular movement. It has an upper frame 12 applied to a patient's head and a lower frame 13 applied to the patient's mandible. There is a plate 14 on upper frame 12 in the vicinity of the patient's tempero-mandibular joint. A measuring device like that illustrated in FIG. 1 is mounted on plate 14. The device can be rotated and displaced in relation to upper frame 12 until its axis coincides with the axis of the joint. A stylus 8 is mounted by a known method on lower frame 13. The position of stylus 8 can be adjusted with mechanical controls. The position of stylus 8 on the measuring device varies with the movement of the patient's mandible and can be electrically determined as described in the foregoing. It is practical to connect a display like an X-Y plotter or oscillograph to the measuring device so that the path followed by the moving joint can be directly visualized. It is, however, just as conceivable to connect a computer to the device to process the results. When the movements of stylus 8 along its axis, which occur in particular when the mandible moves laterally, are also electrically determined, which can be done in a way that is in itself known, an associated computer can be exploited to provide a perspective drawing of the path followed by the moving tempero-mandibular joint, considerably facilitating the diagnosis of various types of disorder and damage. A computer can also be exploited to directly control machine tools to create a simulation of the joint. Simulations of this type can be employed in articulators to imitate the movement of a patient's jaw in a model.

FIG. 4 illustrates another embodiment. The measuring device in this case is connected to a different type of potentiometer circuit with additional resistors. Perforations 7 are oblong slits, some of which are angled.

The measuring device in accordance with the invention can be employed in a very wide range of applications, only some of which are described herein. The device can for example be utilized to pick up manually completed drawings that can then be processed by computer. It is also possible to write on the measuring device, to supply a sample signature for example, with the handwriting thus converted into an electric signal that can be further processed appropriately.

We claim:

1. In an apparatus for measurement of jaw or tempero-mandibular movement, a planar electric measuring apparatus for determining a site whereon a stylus rests comprising: a stylus; an electrically conductive surface positioned below and in contact with said stylus; connection electrodes having contact points applied to said conductive surface, said contact points contacting said surface; said conductive surface having perforations in vicinity of said electrodes for providing said surface with a predetermined electrical field; and means connected between said electrodes and said stylus for determining the position of said system on said conductive surface.

2. Apparatus as defined in claim 1, wherein said electrodes are positioned in pairs with said surface between them.

3. Apparatus as defined in claim 1, wherein said electrodes comprise at least two pairs of electrodes.

4. Apparatus as defined in claim 3, wherein a line connecting said electrodes in one pair intersects a line connecting at least one other pair of electrodes.

5. Apparatus as defined in claim 4, wherein lines connecting the electrodes of two pairs are at a right angle to each other.

6. Apparatus as defined in claim 4, wherein the same arrangement of perforations in the conductive surface is associated with each electrode.

7. Apparatus as defined in claim 6, wherein said electrodes and associated perforations are arranged symmetrically.

8. Apparatus as defined in claim 1, wherein said perforations are positioned substantially between said electrodes.

9. Apparatus as defined in claim 1, wherein said conductive surface comprises resistive film.

10. Apparatus as defined in claim 9, wherein said perforations are circular and are arranged in a triangle in vicinity of said electrodes.

11. Apparatus as defined in claim 10, wherein said surface comprises further means rotatable and displaceable in relation to the upper frame.

12. Apparatus as defined in claim 1, including means for measurement of jaw or tempero-mandibular movement having an upper frame adapted to be applied to a patient's head and a lower frame applied to the patient's mandible, said conductive surface being mounted on said upper frame and said stylus being mounted on said lower frame.

13. Apparatus as defined in claim 10 wherein said surface comprises further magnets for fastening said surface to said upper frame.

14. In an apparatus for measurement of jaw or tempero-mandibular movement, a planar electric measuring apparatus for determining a site whereon a stylus rests comprising: a stylus; an electrically conductive surface positioned below and in contact with said stylus; connection electrodes having contact points applied to said conductive surface, said contact points contacting said surface; said conductive surface having perforations in the vicinity of said electrodes for providing said surface with a predetermined electrical field, said predetermined electrical field comprising a predetermined system of equipotential lines; and means connected between said electrodes and said stylus for determining the position of said stylus on said conductive surface.

* * * * *